(12) United States Patent
Yu et al.

(10) Patent No.: US 9,254,266 B2
(45) Date of Patent: Feb. 9, 2016

(54) INHIBITING SURFACE ENHANCED CRYSTALLIZATION OF AMORPHOUS PHARMACEUTICALS WITH ULTRATHIN COATINGS

(75) Inventors: Lian Yu, Madison, WI (US); Melgardt M. De Villiers, Madison, WI (US); Tian Wu, Thousand Oaks, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1539 days.

(21) Appl. No.: 12/053,244

(22) Filed: Mar. 21, 2008

(65) Prior Publication Data

US 2008/0233157 A1     Sep. 25, 2008

Related U.S. Application Data (60) Provisional application No. 60/896,114, filed on Mar. 21, 2007.

(51) Int. Cl.
| | | |
|---|---|---|
| *A61K 31/4422* | (2006.01) | |
| *A61K 31/405* | (2006.01) | |
| *A61K 9/00* | (2006.01) | |
| *A61K 9/14* | (2006.01) | |

(52) U.S. Cl.
CPC ............... *A61K 9/143* (2013.01); *A61K 9/146* (2013.01); *A61K 31/405* (2013.01); *A61K 31/4422* (2013.01)

(58) Field of Classification Search
None
See application file for complete search history.

(56) References Cited

U.S. PATENT DOCUMENTS

| | | | |
|---|---|---|---|
| 5,773,025 A | | 6/1998 | Baichwal |
| 6,042,847 A | * | 3/2000 | Kerc et al. ............... 424/472 |
| 7,045,146 B2 | | 5/2006 | Caruso et al. |
| 2003/0157260 A1 | | 8/2003 | Rubner et al. |
| 2004/0052847 A1 | * | 3/2004 | Namburi et al. ............... 424/471 |
| 2006/0204533 A1 | | 9/2006 | Hsu et al. |
| 2007/0020469 A1 | | 1/2007 | Wood et al. |

OTHER PUBLICATIONS

Hancock et al. (Pharmaceutical Research, vol. 17, No. 4, 2000).*
Pargaonkar et al. (Pharmaceutical Research vol. 22, No. 5, May 2005).*
Ye et al. (Journal of Controlled Release 106 (2005) 319-328).*
Forster et al., Characterization of glass solutions of poorly water-soluble drugs produced by melt extrusion with hydrophilic amorphous polymers, Journal of Pharmacy and Pharmacology, vol. 53, No. 3, Mar. 2001, pp. 303-315.

* cited by examiner

*Primary Examiner* — David J Blanchard
*Assistant Examiner* — Garen Gotfredson
(74) *Attorney, Agent, or Firm* — Bell & Manning, LLC (57) ABSTRACT

The present invention provides surface-stabilized amorphous pharmaceuticals comprising an amorphous pharmaceutical substrate coated with a biocompatible immobilizing material. Amorphous pharmaceutical substrates that are prone to surface enhanced crystallization benefit from the present coatings. The coated amorphous pharmaceuticals of the present invention maintain their amorphous state and, therefore, their solubility over extended periods of time, relative to uncoated pharmaceuticals.

32 Claims, 8 Drawing Sheets

INHIBITING SURFACE ENHANCED CRYSTALLIZATION OF AMORPHOUS PHARMACEUTICALS WITH ULTRATHIN COATINGS

CROSS-REFERENCE TO RELATED APPLICATION

This application claims the benefit of provisional application No. 60/896,114, filed Mar. 21, 2007, the disclosure of which is incorporated herein by reference.

GOVERNMENT RIGHTS

This invention was made with United States Government support awarded by the following agencies: USDA/CSREES 2005-35503-16303. The United States Government has certain rights in this invention.

FIELD OF THE INVENTION

The present invention relates to methods of inhibiting the surface enhanced crystallization of amorphous pharmaceuticals by coating the amorphous pharmaceuticals with a biocompatible immobilizing material. Also disclosed are the coated amorphous pharmaceuticals.

BACKGROUND OF THE INVENTION

The full potential of many therapeutically important drugs is not realized due to poor solubility of the solid crystalline form of the drug. It is estimated that more than 40% of all drugs discovered have drug delivery limitations due to poor solubility or poor permeability. A variety of approaches have been developed in order to improve the delivery of insoluble drugs, including micronization of the drug, formation of drug nanocrystals, and dispersing the drug in polymers, lipids, or surfactants. Each has met with limited success.

Another way to deliver poorly soluble drugs is to use amorphous solids of the drugs (glasses) instead of the more commonly used crystalline solids. Amorphous solids have liquid-like molecular structures but crystal-like strength and hardness. They are generally more soluble and more bioavailable than their crystalline counterparts. Unfortunately, the amorphous phase for many amorphous substances is unstable and, as a result, many amorphous pharmaceuticals recrystallize over time, leading to a loss in aqueous solubility. Thus, a need exists for a method of preventing or inhibiting the crystallization of amorphous pharmaceuticals.

SUMMARY

The present invention provides surface-stabilized amorphous pharmaceuticals comprising an amorphous pharmaceutical substrate coated with a biocompatible immobilizing material. The amorphous pharmaceutical substrates that benefit from the present coatings are those that are prone to surface enhanced crystallization, as defined below. The coated amorphous pharmaceuticals of the present invention maintain their amorphous state and, therefore, their solubility over extended periods of time, relative to uncoated pharmaceuticals.

The present invention is based, in part, on the discovery that certain amorphous pharmaceutical substrates crystallize faster at the surface than through the bulk. This phenomenon is termed "surface-enhanced crystallization." Surface enhancement exists for nucleation and growth, two elemental steps of crystallization. For amorphous pharmaceuticals, crystal nucleation occurs preferentially at the free surface and crystal growth can be orders of magnitude faster than crystal growth through the bulk. The present invention is further based, in part, on the inventors' discovery that the mechanism of surface enhanced crystallization may be inhibited by certain biocompatible immobilizing materials. Although the present coatings may be beneficial for a variety of amorphous materials, they are particularly well-suited for amorphous pharmaceutical materials that undergo "surface enhanced crystallization.

The coating of a biocompatible immobilizing material may comprise any material that is capable of inhibiting crystallization at the surface of a pharmaceutical substrate. The biocompatible material may prevent crystals from forming on the surface of the coated amorphous pharmaceutical for a period of time and/or reduce the rate of surface enhanced crystallization of the coated amorphous pharmaceutical relative to the rate of surface enhanced crystallization of the uncoated amorphous pharmaceutical. Both the periods of time and the magnitude of the reduction in the rate of surface enhanced crystallization may vary. The coating may be a very thin coating, having a thickness of a few molecular layers of an amorphous substrate that is prone to surface enhanced crystallization.

Non-limiting examples of biocompatible immobilizing materials that may be used as coating include biocompatible metals and polyelectrolytes. In some embodiments, the coating comprises one or more layers of a biocompatible immobilizing material. For example, in some embodiments, the coating comprises a single layer of polyelectrolyte disposed on the amorphous pharmaceutical substrate, while in other embodiments the coating may comprise multiple layers of polyelectrolyte, wherein neighboring layers comprise of oppositely charged (i.e., anionic and cationic) polyelectrolytes.

The thickness of the coatings and the continuity of the biocompatible immobilizing material forming the coating may vary. For example, the coatings may be very thin, having a thickness similar in scale to the thickness of the mobile surface molecule layer of an amorphous substrate that is prone to surface enhanced crystallization. In some embodiments, the coating is from about 1 nm to about 20 nm thick. In other embodiments, the coating is from about 3 nm to about 20 nm thick. In yet further embodiments, the coating is from about 3 nm to about 10 nm thick. The coatings take the form a continuous or discontinuous film of biocompatible immobilizing material deposited over the amorphous pharmaceutical.

In many instances, it is desirable to use a coating that is sufficiently thin so that it does not significantly affect the dissolution rate of the pharmaceutical material. Thus, at a minimum, the dissolution rate should not become so slow that the drug is no longer bioavailable. Indeed, amorphous pharmaceuticals are often favored over their crystalline counterparts because they are significantly more water soluble in aqueous solution. For example, an amorphous pharmaceutical material may have an aqueous solubility that is at least 5 times, at least 10 times, or at least 30 times more than the aqueous solubility of its crystalline counterpart. In some embodiments, the amorphous pharmaceutical has an aqueous solubility of more than 30 mg/mL, while its crystalline counterpart has an aqueous solubility of less than 1 mg/mL. For this same reason, amorphous pharmaceuticals are also generally less desirable than their crystalline counterparts for time-release formulations.

In addition to having enhanced amorphous surface stability, the coated amorphous pharmaceutical substrate of the present invention may be characterized by a variety of improved properties, including, but not limited to, improved wetting ability, improved aqueous dispersibility and/or improved powder flow. In some embodiments, the wetting ability and powder flow of the coated amorphous pharmaceutical is improved as compared to the wetting ability and powder flow of the uncoated amorphous pharmaceutical. In other embodiments, the coated amorphous pharmaceutical is characterized by an intrinsic dissolution rate. In such embodiments, the rate of decrease in the intrinsic dissolution rate of the coated amorphous pharmaceutical is less than the rate of decrease in the intrinsic dissolution rate of the uncoated amorphous pharmaceutical. In other embodiments, the intrinsic dissolution rate of the coated amorphous pharmaceutical remains substantially the same over various periods of time.

Also provided are methods of inhibiting the crystallization of an amorphous pharmaceutical by coating the amorphous pharmaceutical with a biocompatible immobilizing material. The coatings may be applied to the amorphous pharmaceutical prior to the onset of surface crystallization or after surface crystallization has begun. The methods are simple, cost effective, applicable to a wide range of amorphous pharmaceuticals, and may be carried out without the use of surfactants or other components which may be poorly tolerated during chronic use. The disclosed methods are compatible with a variety of coating techniques. For example, a polyelectrolyte coating may be deposited onto a pharmaceutical substrate using layer-by-layer (LbL) deposition techniques. In its basic embodiment, this technique entails forming a first solution of a first polyelectrolyte having a charge opposite to a surface charge on the substrate and exposing the amorphous pharmaceutical substrate to the first solution to form a coated amorphous pharmaceutical. In further embodiments, the technique further comprises forming a second solution of a second polyelectrolyte having a charge opposite to the charge of the first polyelectrolyte and exposing the coated amorphous pharmaceutical to the second solution. This process may be repeated until the desired number of layers have been applied The composition of the polyelectrolyte solutions, the concentration of polyelectrolyte in the solutions, and the length of time the amorphous pharmaceutical is exposed to each solution may vary. For example, the concentration of polyelectrolyte in a particular layer may be the same or different as the concentration of polyelectrolyte in an adjacent layer.

BRIEF DESCRIPTION OF THE DRAWINGS

FIG. 2a is uncoated amorphous IMC on a 15-mm diameter microscope cover glass after 90 hrs at 40° C. The sample in FIG. 2b is the same as in FIG. 2a, 7 days later. FIG. 2c shows crystals of γ IMC in a partially crystallized sample coated with gold. FIG. 2d is the same as FIG. 2c, after 7 days at 40° C. FIG. 2e shows crystals of α IMC in a partially crystallized sample coated with gold. FIG. 2f is the same as FIG. 2e, after 7 days at 40° C.

FIG. 6a shows coated IMC after 20 days at 40° C. while FIG. 6b shows uncoated IMC after 2 days at 40° C.

DETAILED DESCRIPTION

The following terms are used throughout the present disclosure as defined below.

"Biocompatible" means suitable for contact with the tissues of human beings and animals without excessive toxicity, irritation, allergic response, or other possible complications commensurate with a reasonable benefit/risk ratio.

The present invention provides coated amorphous pharmaceuticals comprising an amorphous pharmaceutical and a coating of biocompatible immobilizing material disposed over the amorphous pharmaceutical. The amorphous pharmaceuticals may be those characterized as being prone to surface enhanced crystallization, as described above. By way of non-limiting examples, indomethacin is an amorphous pharmaceutical exhibiting a rate of crystal growth at its free surface which is at least two orders of magnitude faster than in the bulk of the pharmaceutical. The rates of crystal growth at the free surface of nifedipine and tazofelone, two other amorphous pharmaceuticals, are about 10 times and 5 times faster, respectively, than in the bulk.

The amorphous pharmaceuticals of the present invention may or may not have actually undergone surface enhanced crystallization prior to being coated with the biocompatible immobilizing material. In some embodiments, the amorphous pharmaceutical has not undergone surface enhanced crystallization and thus comprises no observable surface crystals prior to the application of the coating. In such embodiments, the biocompatible immobilizing material may prevent crystals from forming on the surface of the coated amorphous pharmaceutical for a period of time. That period of time may vary, but in some embodiments, no observable crystals are formed on the surface of the coated amorphous pharmaceutical for a period of at least one week. In other embodiments, the period of time is at least two weeks, three weeks, or four weeks. In other embodiments, the uncoated amorphous pharmaceutical has undergone some degree of surface crystallization and thus comprises at least some surface crystals, prior to the application of the coating; i.e., the surface of the pharmaceutical is partially crystallized at the time the coating is applied. In these embodiments, the biocompatible immobilizing material reduces the rate of the surface crystallization of the coated amorphous pharmaceutical by a factor ranging from about two to from about 100 or more. As non-limiting examples, for amorphous indomethacin, the biocompatible immobilizing material may reduce the rate of the surface crystallization of the coated amorphous pharmaceutical by a factor of 100 or more. For amorphous nifedipine, the rate may be reduced by a factor of about 10 or more.

A variety of amorphous pharmaceuticals may be used to form the coated amorphous pharmaceuticals. In some embodiments, the amorphous pharmaceuticals comprise drugs, vitamins, nutrients, hormones, growth factors, antibiotics, vaccines, excipients, preservatives, or combinations thereof. Examples of amorphous drugs include, but are not limited to, indomethacin, nifedipine, and tazofelone. The amorphous pharmaceutical substrates may take a variety of forms, including, but not limited to, particles of the active pharmaceutical ingredients and pharmaceutical tablets.

A variety of biocompatible immobilizing materials may be used to coat the amorphous pharmaceuticals, provided the material inhibits the surface crystallization of the amorphous pharmaceutical. In some embodiments, the immobilizing material comprises a biocompatible metal. Useful metals include, but are not limited to gold and silver. The metals may be applied to the pharmaceutical substrates using a variety of techniques. By way of example only, the metal may be deposited over the amorphous pharmaceutical via sputter deposition. However, other well-known metal deposition techniques are compatible with the methods disclosed herein. In other embodiments, the immobilizing material comprises one or more layers of polyelectrolytes. The polyelectrolytes may be cationic or anionic polyelectrolytes, and may be applied to the pharmaceutical substrates using LbL techniques. Useful polyelectrolytes include, but are not limited to, poly(dimethyldiallyl ammonium chloride), poly(allylamine hydrochloride); poly(diallylmethyl ammonium chloride); poly(ethylene imine); polyvinylpyrrolidone, poly-L-ornithine, poly-L-arginine, protamines, chitosan, poly(styrene sulfonate), poly (acrylic acid), polymethacrylic acid, poly(vinylsulfonate), polyphosphoric acid; poly-L-glutamic acid (w), alginates (w), dextran sulphate, carrageenan, nucleic acids, charged dendrimers and charged polymethacrylates. In the case of multi-layered polyelectrolyte coatings, the concentration of the polyelectrolyte solution used to deposit a particular layer may be the same or different from the concentration of the polyelectrolyte solution used to deposit an adjacent layer. In some embodiments, the concentration of the solution for depositing the first polyelectrolyte layer is greater than the concentration of the solution for depositing the second polyelectrolyte layer. The inventors have discovered that such protocol minimizes the crystallization of amorphous pharmaceuticals during coating, which is faster during the coating of the first layer and less significant during the coating of subsequent layers.

The coated amorphous pharmaceuticals of the present invention may be characterized by improvements in various properties, including, but not limited to, wetting ability and powder flow. Typically, the coated amorphous pharmaceuticals exhibit increased wetting ability, as measured by water contact angle, compared to the uncoated amorphous pharmaceuticals. In some embodiments, the water contact angle of the coated amorphous pharmaceutical is from about 10% less to about 40% less than the water contact angle of the uncoated amorphous pharmaceutical. Similarly, the coated amorphous pharmaceuticals typically exhibit increased powder flow, as measured by the angle of repose and/or percent compressibility, compared to the uncoated amorphous pharmaceuticals. In some embodiments, the angle of repose of the coated amorphous pharmaceutical is at least 1.5 times, at least 2 times, or at least 5 times less than the angle of repose of the uncoated amorphous pharmaceutical. In other embodiments, the percent compressibility of the coated amorphous pharmaceutical is at least 1.5 times, at least 2 times, or at least 5 times less than the percent compressibility of the uncoated amorphous pharmaceutical.

The coated amorphous pharmaceuticals may be further characterized by an intrinsic dissolution rate (IDR). It is expected that the IDR of the coated amorphous pharmaceutical may be less than the IDR of the uncoated amorphous pharmaceutical. However, it may be desirable in many instances to maximize the IDR of the coated amorphous pharmaceuticals disclosed herein. The IDR may be maximized by adjusting the composition, coverage and/or thickness of the coating of the biocompatible immobilizing material. Moreover, because the coating of biocompatible immobilizing material inhibits the surface crystallization of an amorphous pharmaceutical, it is generally desirable that the rate of decrease in the IDR of the coated amorphous pharmaceutical due to crystallization be less than rate of decrease in the IDR of the uncoated amorphous pharmaceutical. In other words, over time, an uncoated amorphous pharmaceutical will crystallize, leading to a decrease in IDR. Because crystallization is inhibited in the coated amorphous pharmaceutical, the decrease in IDR over time due to crystallization will be less.

Accordingly, in some embodiments, the increase in intrinsic dissolution rate of the coated amorphous pharmaceutical remains substantially the same over a period of time. By substantially the same, it is meant that the IDR changes by no more than about 10% over a period of at least three weeks when stored at 40° C. In some embodiments, the intrinsic dissolution rate of the coated amorphous pharmaceutical remains substantially the same over a period of at least 6 months when the samples are stored at room temperature.

The present invention, thus generally described, will be understood more readily by reference to the following examples, which are provided by way of illustration and are not intended to be limiting of the present invention.

EXAMPLES

Figure 1:
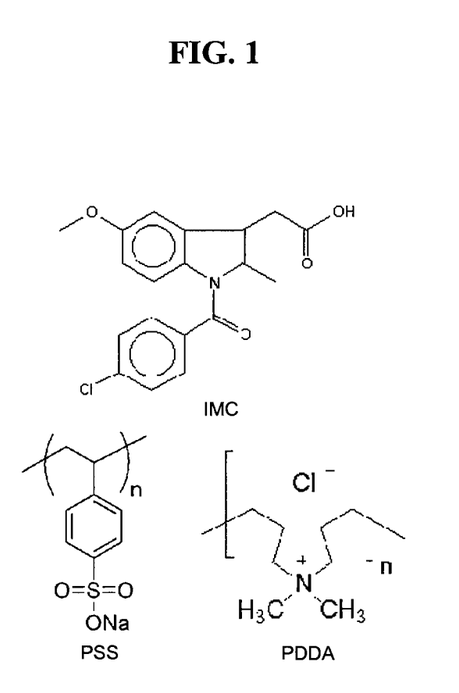
FIG. 1 shows the molecular structures of IMC (1-(p-chlorobenzoyl)-5-methoxy-2-methylindole-3-acetic acid), PDDA (poly(dimethyldiallyl ammonium chloride)), and PSS (sodium poly(styrenesulfonate)).

Materials. Indomethacin [1-p-chlorobenzoyl)-5-methoxy-2-methylindole-3-acetic acid, 99+%, IMC, $\gamma$ polymorph] was obtained from Sigma (St. Louis, Mo.) and used as received. Amorphous IMC was prepared by melting IMC at 175° C. for 5 minutes and quenching to 22° C. Poly(dimethyldiallyl ammonium chloride) (PDDA, MW 100,000-200,000, 20 wt % in water) was obtained from Sigma (St. Louis, Mo.) and sodium poly(styrenesulfonate) (PSS, MW 70,000) from Alfa Aesar (Ward Hill, Mass.). Unused solutions of PDDA or PSS were capable of being stored at 4° C. for up to a week. FIG. 1 shows the molecular structures of IMC, PDDA, and PSS.

Deposition of gold coatings. A Denton Vacuum Desk II (Denton Vacuum, Moorestown, N.J.) was used to deposit a gold coating on amorphous IMC. The conditions used included 50 mTorr pressure, 45 mA current, and 30 s deposition time. Under these conditions, the deposition rate was ca. 10 nm/30 s, providing a gold coating of about 10 nm in thickness. The gold coating was applied to a 15 μm thick amorphous IMC film prepared on a round microscope cover glass attached to a metal stub. The coated film was golden and reflective.

Zeta potentials were measured with a ZetaSizer 3000HSA (Malvern Instruments, USA). Sample particles (ca. 5 mg) were dispersed in 0.01 M NaCl. The measurement was used to determine the surface charge of IMC and follow its reversal as a result of coating with polyelectrolytes of alternating charges. Each reported result was the average of three measurements.

Preparation of LbL polyelectrolyte coating solutions. A 2 mg/ml aqueous solution of PDDA was prepared by dissolving the polymer in Milli-Q water; the solution pH was 6.1. At this pH, PDDA (isoelectric point=12) is positively charged.[21] A 2 mg/ml aqueous solution of PSS was prepared by dissolving the polymer in Milli-Q water; the solution pH was 6.4. At this pH, PSS (isoelectric point=1) is negatively charged.

Deposition of LbL polyelectrolyte coatings on amorphous films. One set of experiments was performed with 15 µm thick amorphous IMC films on microscope cover glasses. Each film was prepared by melting 5 mg of γ IMC at 175° C. for 5 minutes between two microscope cover glasses, cooling the sample to 22° C. ($T_g$−20° C.), and gently removing one cover glass. To coat several films at once, they were loaded into a Teflon rack and immersed into the PDDA solution for 15 minutes. The samples were washed twice in Milli-Q water to remove the excess PDDA and immersed in the PSS solution. This procedure was repeated until the desired number of polymer layers was reached. The coated samples were left on a Whatman filter paper to remove the excess liquid on the slide and dried in a vacuum (0.4 mTorr) at 22° C. for 3 hrs.

Deposition of LbL polyelectrolyte coatings on amorphous particles. To coat amorphous IMC particles, 100 mg amorphous IMC (prepared by melt-quenching) was ground in a mortar with a pestle in the presence of 6 ml of the PDDA solution for 2 minutes. The suspension was transferred to a 1.5 ml Eppendorf tube and, 15 minutes later, centrifuged at 5000 RPM for 30 s (model 5145D, Eppendorf, Westbury, N.Y.). The supernatant was removed and the particles were washed twice with Milli-Q water. The PSS solution was then added to the sample to coat the second layer (coating time=5 minutes). The procedure was repeated until the desired number of layers was reached.

To coat amorphous IMC particles with one layer of PDDA at a larger scale, 2 g of amorphous IMC was loaded into a cryogenic impact mill (model 6750, SPEX CertiPrep, Metuchen, N.J.) and ground with an impact frequency of 10 Hz for 2 minutes with subsequent cooling provided by liquid nitrogen. The particles were sieved through to a 75 µm screen, transferred to a 200 ml beaker containing 100 ml of the PDDA solution, and kept in contact with the solution for 15 minutes. The suspension was filtered through #2 Whatman filter paper to remove the supernatant and washed with Milli-Q water. Vacuum was then applied to dry the particles for at least 3 hrs. TGA showed that on heating to 150° C., the weight loss of the resulting material was about 0.2%.

X-ray powder diffraction (XRPD). XRPD was performed with a Bruker D8 Advance X-ray diffractometer, which was equipped with a CuKα source (λ=1.54056 Å) operating at a tube load of 40 kV and 40 mA. The divergence slit size was 1 mm, the receiving slit, 1 mm, and the detector slit, 0.1 mm. Data was collected by a high-resolution Sol-X detector. Each sample was scanned between 2 and 40° (2θ) with a step size of 0.02° and a maximum scan rate of 3 s/step. The NIST standard SRM 1976 was used to check the instrument's calibration and performance. Samples of small quantities were analyzed on a Si(510) zero-background holder. Polarized light microscopy (PLM) was performed with a Nikon Optiphot Pol 2 microscope equipped with an Olympus video camera. The video image was calibrated against a 1-mm stage micrometer (100 divisions). Differential scanning calorimetry (DSC) was conducted in crimped Al pans using a TA Instruments Q1000 unit under 50 mL/min N2 purge.

Contact Angle Measurements. The measurements were performed at 22° C. and 70% R.H. using a method similar to that of Zografi and Tam. 10 µl of Milli-Q water was deposited on the surface of an amorphous IMC film prepared on a microscope slide. The water droplet thus formed was about 3 mm in diameter. A side view of the droplet was recorded with a digital camera and the contact angle was measured from the image (Image J1.34 S). Each amorphous film was measured three times at different sites. Three samples were measured for each coating condition.

Flowability measurements. To measure the angle of repose, an indicator of flowability, 1.5 g of IMC powder (sieved through to a 75 µm screen) was poured through a funnel with a 9-mm inside diameter and an outlet 1" above the receiving surface. To determine tapped density and compressibility, approximately 1.5 g of powder was poured into a 10-ml cylinder. The initial volume ($V_0$) yielded the initial bulk density $D_0$ ("fluff or poured bulk density"). The powder was then tapped for 5 minutes to obtain the final bulk volume ($V_f$) and the final bulk density $D_f$ ("equilibrium, tapped or consolidated bulk density"). The percent (%) compressibility (Carr's Index) was calculated from $(D_f-D_0)/D_f \times 100$, which is another measure of powder flowability (% compressibility higher than 40% is thought to indicate a non-flowing, cohesive powder; % compressibility lower than 28% is thought to indicate a fluid to free-flowing powder).

Measurement of intrinsic dissolution rate (IDR). The IDR was measured using a USP Dissolution Apparatus II (rotating paddle, model RC-8D, Vanguard, Spring, Tex.) following standard procedures. 250 mg of IMC powder was loaded into a 13-mm diameter steel shaft and compressed into a tablet under a force of 5500 lb for 30 seconds with a single-punch press (model 3890.1D10A00, Carver, Wabash, Ind., USA). Tablets without visible chipping or surface imperfection were used for dissolution measurement. Each tablet used for IDR measurement was coated on one side and around the rim with water-impervious shellac (clear nail polish) that contained as the primary ingredient tosylamide epoxy resin. Conditions of the IDR measurement were as follows: 500 ml of 0.1 M phosphate buffer (pH 7.2), 50 RPM of paddle speed, 1 inch between the tablet and the paddle, and 37° C. Samples were taken every 2.5 minutes up to 15 minutes, every 5 minutes up to 30 minutes, and every 10 minutes up to 60 minutes. Each sample (2 ml) of the solution was drawn with a syringe and filtered through a 0.22-µm filter needle. The sample's concentration was determined by UV-visible spectrometry at 318 nm. The analyzed solution was returned to the dissolution vessel to maintain the constant volume. For each amorphous IMC material studied (with and without coating, with and without aging), the IDR measurement was performed six times with three independently prepared materials as described above. The standard curve for UV-visible spectrometry was obtained by measuring IMC solutions of known concentrations in 0.1 M PBS buffers (pH 7.2). The solubility of γ IMC at 37° C. in the same buffer was determined by measuring the concentration of a 2 mL solution equilibrated with excess γ IMC (shaken for 24-48 hrs until no change of absorbance).

Example 1

Surface Crystallization of Uncoated and Gold-Coated Amorphous IMC Films

Figure 2:
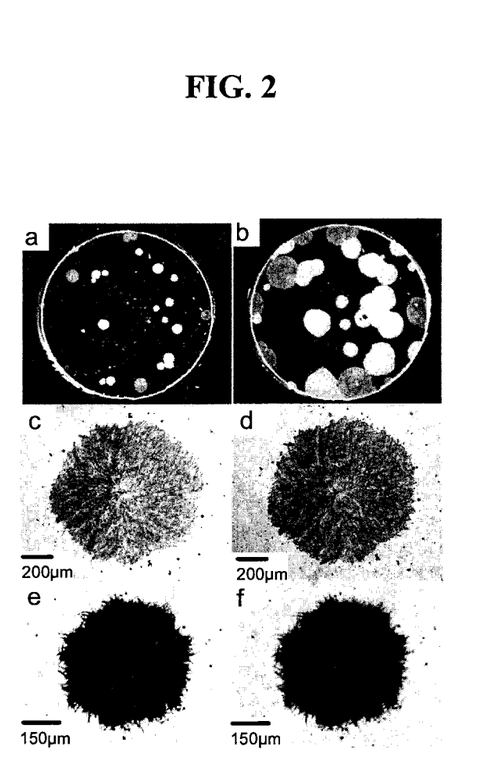
FIG. 2 shows the effect of a 10-nm-thick gold coating on the surface crystallization of amorphous IMC.

Amorphous IMC film prepared between two microscope cover glasses does not crystallize for months below $T_g$ (42° C.). Even in the presence of crystal seeds (introduced by partial melting of crystals and quenching), crystals grow slowly, at ca. $10^{-11.3}$ m/s at 40° C. ($T_g$−2° C.). In contrast, if one of the cover glasses is removed to expose a free surface, crystals appear in days at 40° C., growing at $10^{-8.9}$ m/s in the γ polymorph and $10^{-9.8}$ m/s in the γ polymorph during the first week. The crystals were found to be several µm thick by cross-sectioning. FIG. 2a shows a typical uncoated film after 90 hrs at 40° C.; the round opaque spots are IMC crystals on an otherwise transparent glass film. The crystals were birefringent. FIG. 2b shows the same film after 11 days (7 days after FIG. 2a), in which the crystals had grown larger. After two or three weeks, the surface was fully covered with crystals. A comparison of experiments performed in a vacuum to those performed in a desiccator showed that surface crystallization on uncoated films is unlikely to be a result of moisture adsorption. At 0.4 mTorr and 22° C., the surface crystallization of amorphous IMC occurred similarly as that in the desiccated ambient air, showing the same rate of crystal growth.

FIGS. 2c-f illustrate the effect of a 10-nm gold coating on the surface crystallization of amorphous IMC. All samples were tested at 40° C. in a desiccator. A gold-coated surface of amorphous IMC showed no crystals in 3 weeks. Moreover, coating a partially crystallized sample with gold inhibited further crystallization. FIG. 2c shows a region of γ IMC crystals in a sample that had been stored for 90 hrs (comparable to the uncoated sample of FIG. 2a) and subsequently coated with gold. As shown in FIG. 2d, after another 7 days, the crystals showed no observable growth. FIG. 2e shows a region of a IMC crystals in a sample that had been stored for 90 hours (comparable to the uncoated sample of FIG. 2a) and subsequently coated with gold. As shown in FIG. 2f, after another 7 days, the crystals showed no observable growth. Using 1 μm as the limit of optical resolution, the growth rate of crystals coated with gold is estimated to be $<10^{-11.8}$ M/s. This corresponds to a slowdown of growth by 2-3 orders of magnitude relative to the growth of uncoated crystals ($10^{-8.9}$ for γ IMC and $10^{-9.8}$ m/s for α IMC). Thus, these results show that an ultra-thin coating (10 nm) can inhibit the surface crystallization of amorphous IMC.

Example 2

Figure 3:
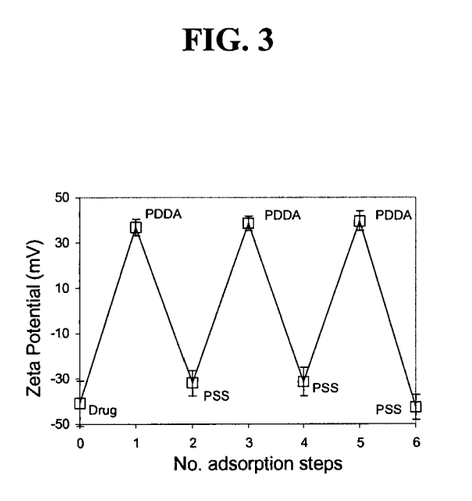
FIG. 3 shows the Zeta potential of amorphous IMC particles versus the number of adsorption steps.

Surface Crystallization of Uncoated and Polyelectrolyte-Coated Amorphous IMC Films Before coating amorphous IMC by this method, the sign of its surface charge in a coating solution was determined. Zeta potential measurements showed that amorphous IMC was negatively charged (ζ-potential=−41 mV, measured as particles suspended in a 0.01 M NaCl). This negative surface charge is consistent with IMC's $pK_a$ (4.5), which ensures that a fraction of IMC molecules are deprotonated at pH≈7. (The pH of the coating solutions was 6.1 (PDDA) and 6.4 (PSS)). Under the same condition, crystalline particles of IMC (γ polymorph) were also negatively charged. Because of this negative charge, the first layer of coating on amorphous IMC was performed with the positively charged PDDA, the next layer with the negatively charged PSS, and so on. FIG. 3, which shows how the zeta potential of amorphous IMC particles changed with the adsorption of alternating layers of PDDA and PSS, confirms deposition of the LbL coating. Coating with one layer of PDDA reversed the surface charge to positive (ζ-potential=+37 mV); adding the next layer (PSS) reversed the surface charge to negative again (ζ-potential=−32 mV); and so on. Finally, when the PDDA and PSS coating solutions were mixed, precipitation occurred, suggesting the feasibility of the layer-by-layer adsorption of polyelectrolytes.

Figure 4:
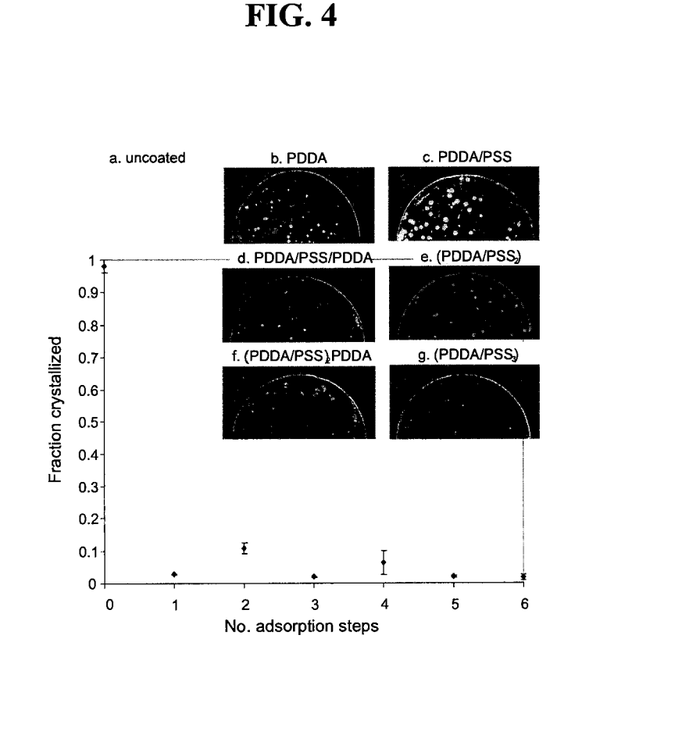
FIG. 4 shows amorphous IMC (15 μm films on 15 mm diameter cover glasses) without and with coating (with PDDA and PSS as indicated) after 20 days at 40° C. White patches or dots are crystals. The plot shows the fraction of surface covered by crystals versus the number of polymer layers.

FIG. 4 shows the effect of the LbL polymer coating on the surface crystallization of amorphous IMC. The set of experiments was again performed with amorphous IMC films prepared on microscope cover glasses. As shown in FIG. 4a, an uncoated surface of IMC was completely covered with crystals in 20 days at 40° C. By contrast, only a small percentage of a coated surface was covered by crystals (white spots in the pictures) under the same conditions (FIG. 4b). Moreover, the crystals that did form on the coated surface grew much more slowly than those on the uncoated surface. Surprisingly, the inhibitory effect was strong even with only one layer of PDDA coating, suggesting that the mobile layer on the surface of amorphous IMC responsible for inducing the surface crystallization is quite thin and, moreover, that thin coatings of polymer serve to immobilize the layer and inhibit crystallization. By comparison, dipping amorphous IMC into the PSS solution alone afforded no inhibition of surface crystallization, probably because the negatively charged PSS is unlikely to deposit on the negatively charged IMC. Finally, FIG. 4 also shows that the number of adsorption steps affects surface crystallization. In particular, inhibition of crystallization was slightly greater for coatings having PDDA as the outer layer, possibly because of interactions between oppositely charged PDDA and PSS that compete with the interactions between PDDA and IMC.

Figure 5:
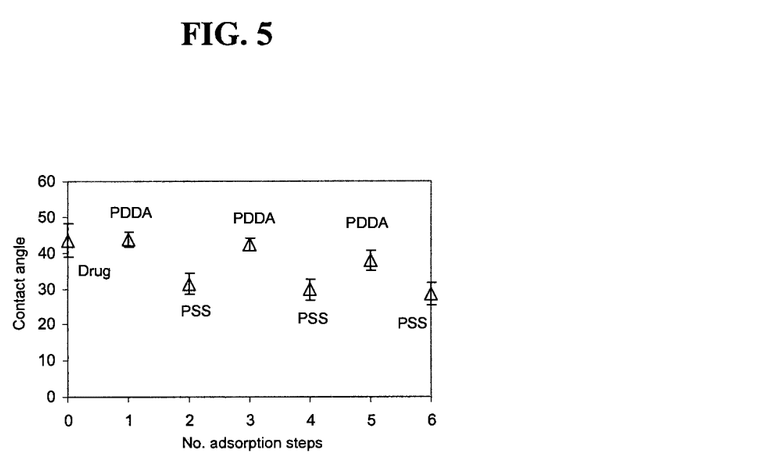
FIG. 5 shows the water contact angle of amorphous IMC film versus the number of adsorption steps.

FIG. 5 shows the effect of the polymer coating on the water contact angle on the surface of amorphous IMC. The water contact angle characterizes the wetting ability of the surface. The measurement was performed with amorphous IMC films on microscope cover glasses. The contact angle on uncoated IMC was 44°. The contact angle did not change significantly with one layer of PDDA, but decreased by 10° with the next layer of PSS. The contact angle increased and decreased accordingly with additional layers of PDDA and PSS. The oscillation of the contact angle confirms that alternative layers of PDDA and PSS have been adsorbed on amorphous IMC and are useful for identifying the particular polymer in the outer layer.

Example 3

Figure 6:
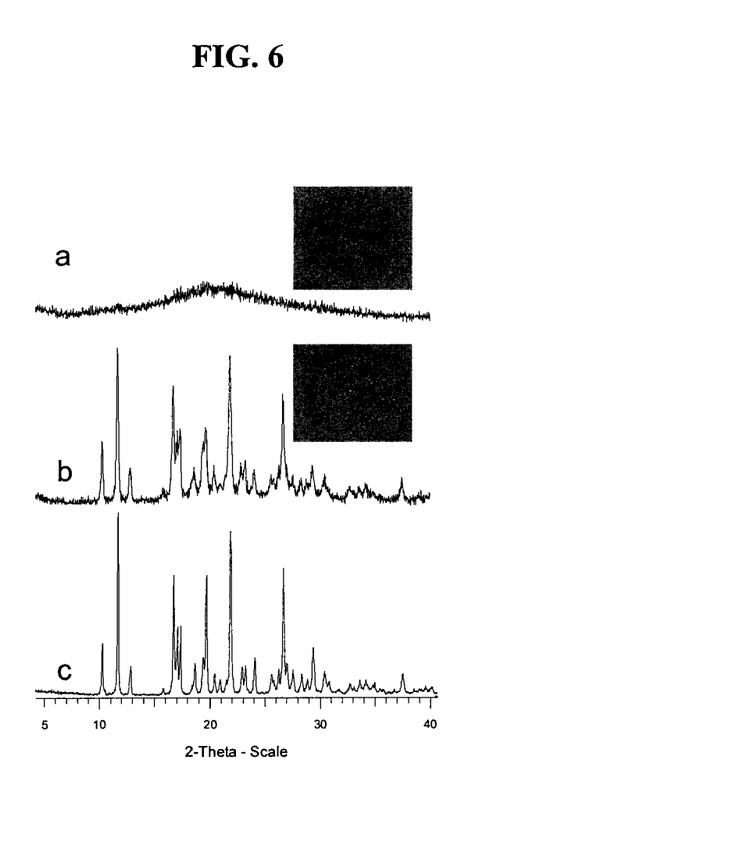
FIG. 6 shows PXRD of coated and uncoated IMC.

Surface Crystallization of Uncoated and Polyelectrolyte-Coated Amorphous IMC Powder FIG. 6 shows the effect a single layer of PDDA on the crystallization of a powder of amorphous IMC (ground and sieved through a screen with 75 μm openings). As shown in FIG. 6b, the uncoated powder crystallized into γ IMC after 2 days at 40° C., changing from yellow (amorphous) to white (crystalline). As shown in FIG. 6a, the coated IMC powder remained amorphous after 20 days at 40° C. and was still yellow.

Figure 7:
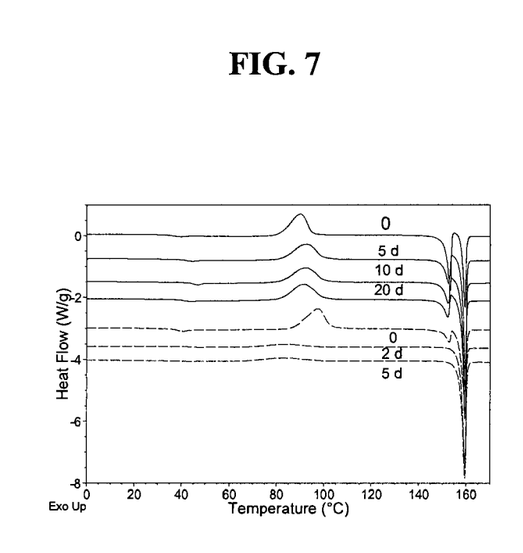
FIG. 7 shows typical DSC traces of coated (top 4 curves) and uncoated (bottom 3 curves) amorphous IMC powder after storage at 40° C. for various days. Scan rate=5° C./minute.

As shown in FIG. 7, a DSC analysis also demonstrates that a PDDA coating inhibits surface crystallization. The crystallization of amorphous IMC, when heated, caused the exotherm to approach 90° C. The larger the exotherm, the greater the amorphous fraction before DSC analysis. For an uncoated powder (the bottom three curves in FIG. 7), the exotherm typically disappears after 2 days of storage at 40° C. By contrast, the exotherm for the coated powder (the top three curves in FIG. 7) was largely unchanged even after 20 days at 40° C., indicating that the coating greatly inhibits crystallization. The slight shifting of the crystallization exotherm was likely a result of the normal variation of nucleation rate in different samples. Moreover, the variation of the glass transition temperature may be a combined result of normal experimental variation and residual moisture in the sample. Finally, the different sizes of the two melting endotherms may be attributed to the fact that crystallization at 40° C. yielded the γ polymorph (FIG. 6), whereas crystallization during the DSC analysis yielded the α polymorph or a mixture of the two.

Physical properties characterizing the flow of amorphous IMC particles, uncoated and coated with a single layer of PDDA are collected in Table 1. Uncoated amorphous IMC powder was cohesive and flowed with difficulty, while the coated powder flowed more easily. For the uncoated powder, the angle of repose was 36°, signifying acceptable flowability. The angle of repose was 18° for the coated IMC, signifying very good flowability.[19] The coating did not significantly change the tapped density, the tablet bulk density (of tablets made with a Carver press), or the porosity. (For these calculations, the true density of 1.31 g/cm$^3$ was used for amorphous IMC.) The coating decreased the powder's % compressibility (Carr's Index), signifying a change from a cohesive, poor-flowing powder (>40%) to an easy-flowing powder.

TABLE 1

Properties of uncoated amorphous IMC powder and amorphous IMC powder coated with a single layer of PDDA.

| | Angle of Repose | Tapped Density (g/cm$^3$) | % Compress-ibility | Tablet Bulk Density (g/cm$^3$) | Tablet Porosity (%) |
|---|---|---|---|---|---|
| Uncoated | 36.1 ± 2.3 | 0.52 ± 0.03 | 42 ± 1 | 1.07 ± 0.03 | 18 ± 2 |
| Coated | 17.8 ± 2.2 | 0.55 ± 0.03 | 24 ± 2 | 1.05 ± 0.02 | 20 ± 1 |

Example 4

Figure 8:
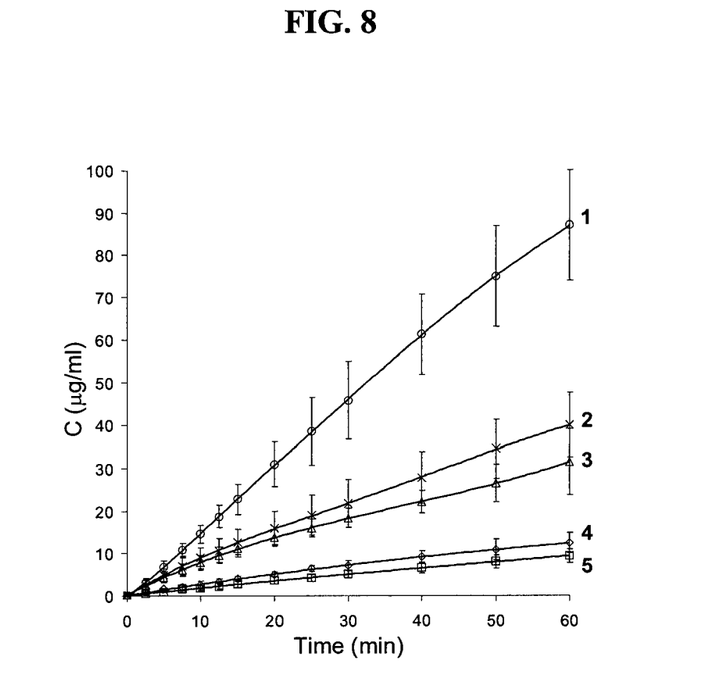
FIG. 8 shows intrinsic dissolution rates of IMC: (1) Amorphous uncoated; (2) Amorphous coated with one layer of PDDA; (3) Same as (2), after 20 days at 40° C.; (4) Same as (1) after 2 days at 40° C.; (5) Crystalline IMC (γ polymorph).

Intrinsic Dissolution Rate of Uncoated and Polyelectrolyte-Coated Amorphous IMC Tablets FIG. 8 and Table 2 show the effect of a polyelectrolyte coating on the intrinsic dissolution rate (IDR) of amorphous IMC. As shown above in FIG. 4, because one layer of PDDA was nearly as effective as several layers of PDDA and PSS in inhibiting surface crystallization, this example used materials coated with a single layer of PDDA. Moreover, thinner coatings are expected to maximize the rate of dissolution. In this example, the IMC powder was compressed into 13-mm diameter tablets about 1.8 mm thick. For comparison, the IDR of γ IMC was also measured. Each data point in FIG. 8 is the average of six measurements. For each sample of amorphous IMC (uncoated or coated), the six measurements were performed with three independently prepared materials (including melting, grinding, coating, and tableting). The solubility of γ IMC in 0.1 M PBS buffer pH 7.2 was determined to be 1.5 mg/ml, which far exceeds the IMC concentration reached during dissolution testing and which ensured a sink condition for the IDR measurement. Similarly, it is assumed that the IDR of amorphous IMC was measured under a sink condition. Because the tablet of amorphous IMC began crystallizing to α IMC in approximately 20 minutes in the dissolution medium, each IDR reported was measured within the first 15 minutes of dissolution.

The IDRs are shown in Table 2. Uncoated amorphous IMC had an IDR 8.0 times that of the crystalline γ IMC (8.0 IDR$_γ$), but the IDR dropped to 1.4 IDR$_γ$ after 2 days of storage at 40° C. due to crystallization. By contrast, the IDR of coated amorphous IMC was 4.7 IDR$_γ$ and only decreased to 4.1 IDR$_γ$ after 20 days at 40° C. Thus, although the polymer coating initially reduced the IDR significantly, that reduced IDR is still much greater than that of γ IMC. In contrast to uncoated IMC, the decrease of IDR due to crystallization over time was significantly slower for the coated material. Specifically, the rate at which the IDR decreased due to crystallization was approximately 100 times slower with coating than without coating.

TABLE 2

Intrinsic dissolution rate (IDR) of amorphous IMC with and without polymer nanocoating.

| | Uncoated | Uncoated 2 d | Coated | Coated 20 d | γ IMC |
|---|---|---|---|---|---|
| IDR (mg/cm$^2$/min) | 0.56 ± 0.12 | 0.10 ± 0.02 | 0.33 ± 0.09 | 0.29 ± 0.04 | 0.07 ± 0.02 |

Example 5

Surface Crystallization of Nifedipine

Nifedipine (dimethyl 2,6-dimethyl-4-(2-nitrophenyl)-1,4-dihydropyridine-3,5-dicarboxylate) is a dihydropyridine calcium channel blocker. The glass transition temperature $T_g$ of amorphous nifedipine is 42° C. The amorphous solid of this drug was made by cooling the nifedipine liquid prepared by melting the crystalline material. Crystallization of the amorphous solid was studied by observing the spontaneous crystallization from the melt using polarized light microscopy. Surface-enhanced crystallization was observed by comparing the crystallization of the material confined between two cover glasses and at a free surface (exposed by removing one of the cover glasses). Crystal growth rate was measured below and above $T_g$ (from 4 to 80° C.). Crystal growth at the free surface was found to be 10 times faster than crystal growth through the bulk. Surface-enhanced crystallization of amorphous nifedipine was inhibited by an ultra-thin coating of gold (10 nm). In coated amorphous nifedipiene, the crystal growth rate slowed approximately to that observed for samples confined between cover glasses.

Example 6

Surface Crystallization of Tazofelone

Tazofelone (5-[(3,5-di-tert-butyl-4-hydroxyphenyl)methyl]-1,3-thiazolidin-4-one) is a potent antioxidant and 5-lipoxygenase inhibitor for treating inflammatory bowel diseases (IBD). The glass transition temperature $T_g$ of amorphous tazofelone is 45° C. The amorphous solid of this drug was made by melting the crystalline material and then cooling to room temperature. The crystallization of the amorphous solid was studied by observing the spontaneous crystallization from the melt using polarized light microscopy. Surface-enhanced crystallization was observed by comparing crystallization of the material confined between two cover glasses and at a free surface (exposed by removing one of the cover glasses). Crystal growth rate was measured below and above $T_g$ (from 4 to 150° C.). Crystal growth at the free surface was found to be approximately 5 times faster than crystal growth through the bulk.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

All publications, patent applications, issued patents, and other documents referred to in this specification are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more."

The invention claimed is:

1. A coated amorphous pharmaceutical comprising:
   (a) an amorphous pharmaceutical, wherein the amorphous pharmaceutical is characterized as being prone to surface enhanced crystallization; and
   (b) a coating of biocompatible immobilizing material comprising a polyelectrolyte, wherein the polyelectrolyte is disposed on the surface of the amorphous pharmaceutical and inhibits the surface enhanced crystallization of the amorphous pharmaceutical; and further wherein no crystallization inhibitor, other than the polyelectrolyte, is disposed on the surface of the amorphous pharmaceutical.

2. The coated amorphous pharmaceutical of claim 1, wherein the amorphous pharmaceutical carries a net charge in pure water.

3. The coated amorphous pharmaceutical of claim 1, wherein the amorphous pharmaceutical has a solubility in water of at least 20 µg/mL.

4. The coated amorphous pharmaceutical of claim 1, wherein the surface of the amorphous pharmaceutical is partially crystallized.

5. The coated amorphous pharmaceutical of claim 1, wherein the amorphous pharmaceutical comprises a drug selected from indomethacin, nifedipine, and tazofelone.

6. The coated amorphous pharmaceutical of claim 1, wherein the biocompatible immobilizing material comprises one or more layers of polyelectrolyte.

7. The coated amorphous pharmaceutical of claim 6, wherein the polyelectrolyte is selected from poly(dimethyldiallyl ammonium chloride) and sodium poly(styrene sulfonate).

8. The coated amorphous pharmaceutical of claim 6, wherein the thickness of the one or more layers of polyelectrolyte is from about 3 nm to about 20 nm.

9. The coated amorphous pharmaceutical of claim 6, wherein the coating comprises a first layer of a first polyelectrolyte disposed on the surface of the amorphous pharmaceutical and a second layer of a second polyelectrolyte disposed on the first layer, wherein the first polyelectrolyte and the second polyelectrolyte are oppositely charged.

10. The coated amorphous pharmaceutical of claim 1, wherein the rate of surface enhanced crystallization of the coated amorphous pharmaceutical is reduced by a factor ranging from about two to from about 1000 times the rate of surface enhanced crystallization of the uncoated amorphous pharmaceutical.

11. The coated amorphous pharmaceutical of claim 1, wherein the coated amorphous pharmaceutical is characterized by an intrinsic dissolution rate and the intrinsic dissolution rate remains substantially the same over a period of at least one week.

12. A coated amorphous pharmaceutical comprising:
   (a) an amorphous pharmaceutical, wherein the surface of the amorphous pharmaceutical is partially crystallized; and
   (b) a coating of biocompatible immobilizing material comprising a polyelectrolyte, wherein the polyelectrolyte is disposed on the surface of the amorphous pharmaceutical and inhibits further crystallization of the amorphous pharmaceutical; and further wherein no crystallization inhibitor, other than the polyelectrolyte, is disposed on the surface of the amorphous pharmaceutical.

13. The coated amorphous pharmaceutical of claim 12, wherein the coating is from about 3 nm to about 20 nm thick.

14. A method of inhibiting the crystallization of an amorphous pharmaceutical comprising depositing a biocompatible immobilizing material comprising a polyelectrolyte onto the surface of an amorphous pharmaceutical, wherein the amorphous pharmaceutical is characterized as being prone to surface enhanced crystallization and the polyelectrolyte inhibits the surface enhanced crystallization of the amorphous pharmaceutical; and further wherein no crystallization inhibitor, other than the polyelectrolyte, is disposed on the surface of the amorphous pharmaceutical.

15. The method of claim 14, further comprising forming a first solution of a first polyelectrolyte and exposing the amorphous pharmaceutical to the first solution to form a layer of the first polyelectrolyte on the surface of the amorphous pharmaceutical, wherein the concentration of the first polyelectrolyte is sufficient to prevent crystallization of the amorphous pharmaceutical during coating.

16. The method of claim 15, further comprising forming a second solution of a second polyelectrolyte and exposing the amorphous pharmaceutical having the layer of first polyelectrolyte on its surface to the second solution to form a layer of the second polyelectrolyte on the layer of first polyelectrolyte.

17. The method of claim 14, wherein the amorphous pharmaceutical carries a net charge in pure water.

18. The method of claim 14, wherein the amorphous pharmaceutical is selected from indomethacin, nifedipine, and tazofelone.

19. The method of claim 14, wherein the surface of the amorphous pharmaceutical is partially crystallized.

20. The method of claim 14, wherein the polyelectrolyte is poly(dimethyldiallyl ammonium chloride) or sodium poly(styrene sulfonate).

21. The method of claim 14, wherein the biocompatible immobilizing material comprises one or more layers of polyelectrolyte and the thickness of the one or more layers of polyelectrolyte is from about 3 nm to about 20 nm.

22. The coated amorphous pharmaceutical of claim 1, wherein the coated amorphous pharmaceutical is characterized by an intrinsic dissolution rate, and further wherein the coating reduces the rate of decrease of the intrinsic dissolution rate relative to the rate of decrease of the intrinsic dissolution rate of the pharmaceutical in the absence of the coating, such that after aging for 2 days at 40° C., the coated amorphous pharmaceutical has a higher intrinsic dissolution rate, when measured using the same experimental conditions and apparatus, than the pharmaceutical in the absence of the coating.

23. The coated amorphous pharmaceutical of claim 22, wherein the rate of decrease in the intrinsic dissolution rate for the coated amorphous pharmaceutical is at least 100 times slower than the rate of decrease in the intrinsic dissolution rate for the pharmaceutical in the absence of the coating.

24. The coated amorphous pharmaceutical of claim 22, wherein the coated amorphous pharmaceutical is characterized by an intrinsic dissolution rate that changes by no more than about 10% after a period of three weeks of storage at 40° C., as measured by a USP Dissolution Apparatus II with a paddle speed of 50 RPM in 500 ml of 0.1 M phosphate buffer solution at 37° C.

25. The coated amorphous pharmaceutical of claim 1, wherein the coated amorphous pharmaceutical comprises no observable surface crystals.

26. The coated amorphous pharmaceutical of claim 6, wherein the coated amorphous pharmaceutical is characterized by an intrinsic dissolution rate, and further wherein the coating reduces the rate of decrease of the intrinsic dissolution rate relative to the rate of decrease of the intrinsic dissolution rate of the pharmaceutical in the absence of the coating, such that after aging for 2 days at 40° C., the coated amorphous pharmaceutical has a higher intrinsic dissolution rate, when measured using the same experimental conditions and apparatus, than the pharmaceutical in the absence of the coating.

27. The method of claim 14, wherein the coating is applied prior to the onset of observable surface crystallization of the amorphous pharmaceutical.

28. The method of claim 14, wherein the coated amorphous pharmaceutical is characterized by an intrinsic dissolution rate, and further wherein the coating reduces the rate of decrease of the intrinsic dissolution rate relative to the rate of decrease of the intrinsic dissolution rate of the pharmaceutical in the absence of the coating, such that after aging for 2 days at 40° C., the coated amorphous pharmaceutical has a higher intrinsic dissolution rate, when measured using the same experimental conditions and apparatus, than the pharmaceutical in the absence of the coating.

29. The coated amorphous pharmaceutical of claim 6, wherein the coating is from about 1 to about 20 nm thick.

30. The coated amorphous pharmaceutical of claim 6, comprising a polyelectrolyte selected from the group consisting of poly(allylamine hydrochloride), poly(diallylmethyl ammonium chloride), poly(ethylene imine), polyvinylpyrrolidone, poly-L-ornithine, poly-L-arginine, a protamine, chitosan, a poly(acrylic acid), polymethacrylic acid, poly(vinylsulfonate), polyphosphoric acid, poly-L-glutamic acid, an alginate, dextran sulphate, and carrageenan.

31. The coated pharmaceutical of claim 1, wherein the coating of biocompatible immobilizing material that inhibits the surface enhanced crystallization of the amorphous pharmaceutical consists essentially of one or more layers of polyelectrolyte.

32. The coated pharmaceutical of claim 1, wherein the coating of biocompatible immobilizing material that inhibits the surface enhanced crystallization of the amorphous pharmaceutical comprises one or more layers of polyelectrolyte that form a continuous film on the surface of the amorphous pharmaceutical.

\* \* \* \* \*